(12) United States Patent
Adams et al.

(10) Patent No.: US 6,747,063 B2
(45) Date of Patent: Jun. 8, 2004

(54) COMBINATION THERAPY FOR TREATMENT OF ERECTILE DYSFUNCTION

(75) Inventors: Michael A. Adams, Kingston (CA); Jeremy P. W. Heaton, Gananoque (CA); Donald H. Maurice, Kingston (CA)

(73) Assignee: Cellegy Pharmaceuticals, Inc., South San Francisco, CA (US)

(*) Notice: Subject to any disclaimer, the term of this patent is extended or adjusted under 35 U.S.C. 154(b) by 0 days.

(21) Appl. No.: 09/177,711

(22) Filed: Oct. 23, 1998

(65) Prior Publication Data
US 2001/0039257 A1 Nov. 8, 2001

Related U.S. Application Data

(63) Continuation of application No. PCT/CA97/00264, filed on Apr. 23, 1997.

(30) Foreign Application Priority Data

Apr. 23, 1996 (GB) ............................................. 9608482

(51) Int. Cl.[7] .................... A61K 31/557; A61K 38/00; A61K 31/195; A61K 31/13
(52) U.S. Cl. ............................ 514/573; 514/2; 514/12; 514/562; 514/645
(58) Field of Search ............................ 514/2, 12, 562, 514/645, 573

(56) References Cited

U.S. PATENT DOCUMENTS

| | | | | |
|---|---|---|---|---|
| 5,217,953 A | * | 6/1993 | Gozes et al. | 514/12 |
| 5,278,192 A | | 1/1994 | Fung et al. | 514/645 |
| 5,380,758 A | * | 1/1995 | Stamler et al. | 514/562 |
| 5,439,938 A | | 8/1995 | Snyder et al. | 514/565 |
| 5,849,803 A | * | 12/1998 | Kock et al. | 514/724 |
| 5,877,216 A | | 3/1999 | Place et al. | |
| 6,306,841 B1 | | 10/2001 | Place et al. | |

FOREIGN PATENT DOCUMENTS

| | | | |
|---|---|---|---|
| WO | WO-9404120 A | * | 3/1994 |
| WO | WO 94/16729 | | 8/1994 |
| WO | WO 96/32118 | | 10/1996 |

OTHER PUBLICATIONS

Medline Abstract, AN 95174112, Akkus et al. 1995.*
Anfossi et al. "Effect of Forskolin and Organic Nitrate on Agregation and intracelluar Cyclic Nucleotide Content in Human Platelets" 1994, General Pharmacology, 25(6), p1093–1100.*

(List continued on next page.)

Primary Examiner—Shengjun Wang
(74) Attorney, Agent, or Firm—Towsend and Towsend and Crew LLP (57) ABSTRACT

In the field of treatment of erectile dysfunction there is disclosed a novel therapy in which the actions of an agent or agents, produce a combination of effects to induce effective erection (and avoid priapism) while reducing or entirely avoiding pain. The method taught combines a first action of an agent which is to antagonize a drug-induced pain stimulus within nociceptive nerves of penile tissue with a second action of either the same agent or of a second agent, which enhances, synergistically, smooth muscle relaxation. The synergism allows for at least an equivalent effect of smooth muscle relaxation to be obtained at significantly lower doses of a smooth muscle relaxing agent such as PGE1 which in standard therapy is also in 40–45% of cases pain-inducing at doses which achieve effective erection. Thus in an anatomical site where nociceptive tissue is in close proximity to one or more effector systems, the method enhances the effector system while reducing nociception in the nociceptive tissue which nociception would be caused by an agent such as PGE1 which is used to trigger the effector system.

20 Claims, 1 Drawing Sheet

OTHER PUBLICATIONS

Campbell et al., "Prevention of Tolerance to Nitroglycerin Patches by Overnight Removal," *Am J Cardiol*, 60:271–275 (1987).

Parker, "Nitrate Tolerance," *Am J Cardiol*, 56:281–311 (1985).

Packer et al., "Hemodynamic Factors Limiting the Response to Transdermal Nitroglycerin in Severe Chronic Congestive Heart Failure," *Am J Cardiol*, 57:260–267 (1986).

Flaherty, "Hemodynamic Attenuation and the Nitrate–Free Interval: Alternative Dosing Strategies for Transdermal Nitroglycerin," *Am J Cardiol*, 56:321–371 (1985).

Armstrong et al., "Blood Levels After Sublingual Nitroglycerin," *Circulation*, 59(3):585 (1979).

Nabel et al., "Effects of Dosing Intervals on the Development of Tolerance to High Dose Transdermal Nitorglycerin," *Am J Cardiol*, 63:663–669 (1989).

Lin et al., "Crossover from Intravenous to Transdermal Nitroglycerin Therapy in Unstable Angina Pectoris," *Am J Cardiol*, 56:742–748 (1985).

Linet, Otto I. et al., "Efficacy and Safety of Intracavernosal Alprostadil in Men with Erectile Dysfunction, " *New England Journal of Medicine*, 334(14):873–877 (1996).

Padma–Nathan, Harin et al., "Treatment of Men with Erectile Dysfunction with Transurethral Alprostadil," *New England Journal of Medicine* 336(1):1–7 (1997).

Ferreira, Sérgio H. et al., "The molecular mechanism of action of peripheral morphine analgesia: stimulation of the cGMP system via nitric oxide release," *European Journal of Pharmacology* 201:121–122 (1991).

Brock, Gerarld et al., "Intracavernous Sodium Nitroprusside: Inappropriate Impotence Treatment," *Journal of Urology* 150:864–867 (1993).

Duarte, I.D.G. et al., "Peripheral analgesia and activation of the nitric oxide–cyclic GMP pathway," *European Journal of Pharmacology*, 186:289–293 (1990).

Ferreira, Sertgio H. et al., "Blockade of hyperalgesia and neurogenic oedema by topical application of nitroglycerin," *European Journal of Pharmacology*, 217:207–209 (1992).

Duarte, Igor D.G. et al., "Analgesia by direct antagonism of nociceptor sensitization involves the arginine–nitric oxide–cGMP pathway," *European Journal of Pharmacology*, 217:225–227 (1992).

Maurice, D.H. and Haslam, R.J. "Molecular Basis of the Synergistic Inhibition of Platelet Function by Nitrovasodilators and Activators of Adenylate Cyclase: Inhibition of Cyclic AMP Breakdown by Cyclic GMP," *Molecular Pharmacology*,37(5):671–681 (1990).

Maurice, Donald H. et al., "Synergistic actions of nitrovasodilators and isoprenaline on rat aortic smooth muscle," *European Journal of Pharmacology*, 1992:235–242 (1991).

Maurice, Donald H. and Haslam, Richard J., "Nitroprusside enhances isoprenaline–induced increases in cAMP in rat aortic smooth muscle," *European Journal of Pharmacology*, 191:471–475 (1990).

Jang, Elliott K. et al., "Synergistic inhibitory effects of atriopeptin II and isoproterenol on contraction of rat aortic smooth muscle: roles of cGMP and cAMP," *European Journal of Pharmacology*, 250:477–481 (1993).

von Heyden, Burkhard et al., "Intracavernous Pharmacotherapy for Impotence: Selection of Appropriate Agent and Dose," *Journal of Urology*,149:1288–1290 (1993).

Hempelmann, Ralf, G. et al., "Non–synergistic relaxant effects of vasoactive intestinal polypeptide and SIN–1 in human isolated cavernous artery and corpus cavernosum," *European Journal of Pharmacology* 276:277–280 (1995).

Martinez–Pineiro, Luis et al., "Preliminary Results of a Comparative Study with Itracavernous Sodium Nitroprusside and Prostaglandin E1 in Patients with Erectile Dysfunction," *Journal of Urology* 153:1487–1490 (1995).

Sun,, Jim X. et al., "Comparative Pharmacokinetics and Bioavailability of Nitroglycerin and its Metabolites from Transderm–Nitro, Nitrodisc, and Nitro–Dur II Systems Using a Stable–Isotope Technique," *J. Clin. Pharmacol.* 35:390–397 (1995).

Strejan, G.H. et al., "Suppression of Chronic–Relapsing Experimental Allergic Encephalomyelitis in Strain–13 Guinea Pigs by Administration of Liposome–Associated Myelim Basic Protein," *Journal of Neuroimmunology* 7:27–41 (1984/1985).

Heaton, J.P.W. et al., "Topical Glyceryltrinitrate Causes Measurable Penile Arterial Dilation in Impotent Men," *Journal of Urology* 143:729–731 (1990).

Kim, Noel N. et al., "Altered Contractility of Rabbit Penile Corpus Cavernosum Smooth Muscle by Hypoxia," *Journal of Urology* 155:772–778 (1996).

* cited by examiner

COMBINATION THERAPY FOR TREATMENT OF ERECTILE DYSFUNCTION

RELATED APPLICATIONS

This application is a U.S. Continuation application which claims priority to international application PCT/CA97/00264, filed on Apr. 23, 1997, which claims priority to United Kingdom provisional application Serial No. 9608408.2, filed on Apr. 23, 1996, now abandoned, the contents of both applications which are incorporated herein by reference in their entirety.

FIELD OF THE INVENTION

The field of invention is the treatment of erectile dysfunction. In particular, the subject matter of this invention consists of a novel and effective treatment of erectile dysfunction using an agent or agents with actions which combine the properties of (a) preventing the induction of pain and (b) reducing the potential for priapism with enhanced capacity for corpus cavernosal smooth muscle relaxation (penile erection).

BACKGROUND OF THE INVENTION

Erectile dysfunction (ED) is a significant clinical problem which occurs in up to thirty percent of males in North America. Causes of impotence are usually divided into two nonexclusive categories, namely, organic and psychological. Organic aspects of ED are typically caused by underlying vascular disease such as that associated with hypertension or diabetes mellitus, can be caused by prescription medications and may include psychiatric disease such as depression. Psychological factors include fear, performance anxiety and interpersonal conflict. ED impairs sexual performance, diminishes self-esteem and disrupts personal relationships (Padma-Nathan, et al NEJM, Vol. 336 (1):1, 1997).

The human male penis is composed of erectile tissue called the corpus cavernosum and corpus spongiosum. The corpus cavernosum is comprised of two segments or erectile bodies each located adjacent to the urethra (or the corpus spongiosum). The erectile tissue is composed of large venous sinuses which contain relatively little blood when the penis is not in the relaxed state but which become very engorged by blood when dilated (relaxed). The dilation of these tissues contributes directly to penile erection.

The stimulus for a physiological erection originates in the central nervous system. A fully functional natural penile erection requires co-ordinated change in output from various levels of the central nervous system and at least three sets of peripheral nerves (thoracolumbar sympathetic, sacral parasympathetic, and pelvic somatic). At the level of penile tissue, localization of sympathetic and parasympathetic as well as non-adrenergic, non-cholinergic nerve terminals has indicated the potential involvement of numerous neurotransmitter systems. A penile erection is known to be dependent upon the balance and integration between structural (vascular and extracellular matrix) and functional control systems (neural, local factors and humoral/endocrine). The nature of the balance between these contributing influences is ultimately expressed as vasodilation and penile tumescence, as long as there is an adequate level of systemic blood pressure and an appropriate hormonal milieu. The penile vascular components that have a significant role in regulating erectile function are the pudendal arterial system, the cavernous arteries, the corpora cavernosa and the corpus spongiosum and glans.

It is well established that an erection requires a neurally mediated (autonomic) vasodilation of both the penile arterial blood vessels and the trabecular meshwork. The combined dilatation facilitates an initial rapid increase in arterial inflow into the cavernous bodies of the penis, promoting tumescence. This is followed by a phase of decreasing inflow as the corporal tissue expands and compresses subtunical veins. This is described as the "veno-occlusive mechanism", and this imposes a dramatic increase in inflow resistance which is required to achieve penile rigidity. Conversely, detumescence is likely mediated, at least in part, by activation of the sympathetic nervous system as well as removal of active vasodilator tone. In addition, it may involve changes in local systems.

One of the widely accepted interventions used in the diagnosis and pharmacological management of erectile dysfunction involves direct injection of a wide range of vasoactive substances into the corpus cavernosum (penis) for the purposes of producing an erection (intra cavernosal "IC" injections). Newer strategies involve the delivery of a similar range of drugs to the urethra (then to the corpus cavernosum by natural mechanisms) with similar consequences. The currently accepted injectable products are not optimal. Two serious adverse reactions associated with these agents are drug-induced pain and priapism (i.e., erections of inappropriate overlong duration) (Linet et al, NEJM, Vol. 334:873 (1996)). It is now known and has been documented in the literature that a single use of prostaglandin E1 (PGE1) produces a pain response in about 3 to 10 percent of individuals using this therapy. However, it also known that over time the repeated use of PGE1 is associated with a continuing incidence of pain. This is such that 40 to 45 percent of patients using PGE1 multiple times will report a pain response with use (Linet et al, NEJM, Vol 334 (14) 873 (1996)). When such patients use PGE1 for a prolonged period of time, they expect that they may experience pain and this becomes a serious problem which may result in decreased use of PGE1 or switching to an alternative therapy. Alternatives currently include surgical intervention (destructive and irreversible, with a success rate between 31 to 80 percent); vacuum devices (moderate efficacy, may be difficult for some men to use and may cause penile trauma); and oral medications (unproven efficacy). Transurethral administration of PGE1 or other vasoactive agents is another alternative approach to injection therapy, although it has resulted in report of penile pain in 35.7 percent of men who attended for clinic testing (Padma-Nathan et al, NEJM, Vol. 336(1): 1 (1997)). At present it is our understanding only two products are approved by the United States FDA for the treatment of ED: intracavernosal injection using PGE1 (Caverject, Upjohn Pharmaceutical; Virilan, Schwarz Pharma) and intraurethral PGE1 (MUSE, Vivus Inc. Menlo Park, Calif.). Thus there is a need to provide a method or therapy for inducing effective erections (and avoid priapism) while reducing or entirely avoiding pain.

SUMMARY OF INVENTION

The present invention is a therapy in which the combination of actions of an agent or agents induce effective erections (and avoid priapism) while reducing or entirely avoiding pain.

According to one aspect of the present invention there is provided a method of augmenting the actions of cyclic adenosine monophosphate (cAMP) in an effector system while reducing cAMP action in a nociceptive system which method comprises application of one or more of the various forms of NO, or CO, to a site wherein the said cAMP exists.

According to another aspect of the present invention, a method is provided wherein alteration of the actions of cAMP is caused by application of an agent which increases cyclic guanosine monophosphate (cGMP).

According to another aspect of the present invention, a method is provided wherein alteration of the actions of cAMP is caused by application of an agent which inhibits phosphodiesterase.

In yet a further aspect of the present invention there is provided, in an anatomical site where nociceptive tissue is in close proximity to one or more effector systems, a method for enhancing said effector system while reducing nociception in said nociceptive tissue comprising modifying the actions of cAMP at said site by application of one or more of the various forms of NO or CO, or comprising application of an agent or agents that potentiate or augment the action of cAMP in said effector systems and in said nociceptive tissue, causing an increase of cGMP relative to cAMP, which would include an overall reduction in cAMP but with relatively more cGMP. The penis and clitoris are examples of such anatomical sites.

According to one aspect of the present invention there is provided a method of enhancing penile erection with minimal or no pain by use of one or more agents that can augment or potentiate the effect of cAMP as well as augment or potentiate the effect of cGMP in both smooth muscle and nerves, irrespective of whether the effect is mediated by changes in the adenylyl or guanylyl cyclase systems or by direct action of NO or CO, or the cyclic nucleotide phosphodiesterases which inactivate these cyclic nucleotides.

According to yet a further aspect of the present invention there is provided a method of enhancing penile erection with minimal or no pain by use of an agent which directly or indirectly generates NO and which augments or potentiates the effect of cAMP in smooth muscle but not in nerves.

According to a further aspect of the present invention there is provided a method for enhancing penile erection with minimal or no pain by use of an agent which generates NO in both smooth muscle and nerves in combination with an agent that augments or potentiates the effect of cAMP in smooth muscle but not in nerves.

According to yet a further aspect of the present invention there is provided a method of enhancing penile erection with minimal or no pain by use of any one of the following NO donors: gylceryl trinitrate, isosorbide 5-mononitrate, isosorbide dinitrate, pentaerythritol tetranitrate, erythrityl tetranitrate, sodium nitroprusside, 3-morpholinosydnonimine molsidomine, S-nitroso-N-acetylpenicillamine, Snitrosoglutathione, N-hydoxy-L-arginine, S,S-dinitrosodithiol, or NO gas, or a functional equivalent thereof in combination with an agent that augments or potentiates the effect of cAMP in smooth muscle but not in nerves.

According to a further aspect of the present invention there is provided a method of enhancing penile erection with minimal or no pain by use of one or more agents which generate NO or CO and which augment or potentiate the effect of cAMP in smooth muscle but not in nerves.

According to a further aspect of the present invention there is provided a method of enhancing penile erection with minimal or no pain by use of an agent which generates NO in both smooth muscle and nerves in combination with an agent that augments or potentiates the effect of cAMP in smooth muscle but not in nerves.

According to a further aspect of the present invention there is provided a method of enhancing penile erection with minimal or no pain by use of at least any one of the following NO donors: glyceryl trinitrate, isosorbide 5-mononitrate, isosorbide dinitrate, pentaerythritol tetranitrate, erythrityl tetranitrate, sodium nitroprusside, 3-morpholinosydnonimine molsidomine, S-nitroso-N-acetylpenicillamine, S-nitrosoglutathione, N-hydroxy-L-arginine, S,S-dinftrosodithiol, or NO gas, or functional equivalents thereof, in combination with an agent that augments or potentiates the effect of cAMP in smooth muscle but not in nerves.

According to a further aspect of the present invention there is provided a method of enhancing penile erection with minimal or no pain by use of any one of the following NO donors: glyceryl trinitrate, isosorbide 5-mononitrate, isosorbide dinitrate, pentaerythritol tetranitrate, erythrityl tetranitrate, sodium nitroprusside, 3-morpholinosydnonimine molsidomine, S-nitroso-N-acetylpenicillamine, S-nitrosoglutathione, N-hydroxy-L-arginine, S,S-dinitrosodithiol, or NO gas, or functional equivalents thereof, in combination with PGE1 or other prostaglandin.

In yet a further aspect of the present invention there is provided a method of enhancing penile erection with minimal or no pain whereby these agents are delivered by any route that will affect penile smooth muscle.

It is a further aspect of the present invention that the methods of this invention are not specific to the penis in that the mechanism is relevant to other systems where avoidance of nociception and enhancement of efficacy are important. For example, regional or generalized pain managed by opiates would be offset by addition of NO generating or active (single agent or combined) compounds that alter relative cAMP and cGMP activation.

The pain reduction of the present invention is hypothesized to result from two independent events which involve actions in two different cellular systems (nerves and smooth muscle). Our idea is to combine a first action which is to antagonize the drug-induced pain stimulus within nociceptive nerves and a second action which is to enhance, synergistically, smooth muscle relaxation. This synergism allows for at least an equivalent effect to be obtained at significantly lower doses of the pain-inducing agent (e.g. PGE1) again reducing the potential for pain.

We further expect that the novel therapeutic strategy of the present invention results in a decrease in pain induced by cAMP elevating agents (e.g. PGE1). We believe that this is accomplished by the antinociceptive actions of increases in levels of cGMP and or NO and or CO and or relative activities in cAMP and cGMP systems in nociceptive nerves mediated by the second agent (or by a second action of the same agent (Ferreira et al, European Journal of Pharmacology 201:121 (1991)). We believe that the combined actions of agent(s) which simultaneously increase both cAMP and cGMP and appear therefore to result in synergistic enhancement in the smooth muscle in those studies, also result in synergistic enhancement of the corpus cavernosal relaxation and hence the erectile response. Note however that the combined actions of the agent(s) in the two tissues are in direct contrast: in nerves the effects of cGMP are antagonistic to the actions of cAMP while in smooth muscle cGMP directly potentiates the effects of cAMP. Notwithstanding this, surprisingly in corpus cavernosal tissue no pain has been observed with such combinations.

A specific example of this invention, described herein, includes the use of a combination of an agent which activates the adenylyl cyclase system (PGE1) and an agent which can both activate the guanylyl cyclase system (sodium nitroprusside-SNP) as well as other systems acting independently of guanylyl cyclase. Alone each of these agents causes smooth muscle relaxation. PGE1 alone, at concentrations which cause smooth muscle relaxation, also can induce hyperalgesia (i.e. pain in approximately 40–45% of patients causing discontinuation of use). SNP injected alone into the penis appears not to induce pain but at doses required to produce consistent penile erections does suffer from a serious side effect of unacceptable systemic hypotension. Typical clinically effective doses for PGE1 monotherapy are between 5 and 20 μg. SNP alone has been shown to produce inadequate penile erections at doses of 50 μg whereas approaching 200 μg it will induce erections but with the significant systemic side effects (Brock et al J. Urology, Vol. 150:864, 1993). We demonstrate below, use of a low dose (5 μg) or moderate dose (15 μg) of PGE1 combined with a low dose SNP (50 μg) to achieve effective erection with no pain.

Definitions

GTN=glyceryl trinitrate
ISMN=isosorbide 5-mononitrate
ISDN=isosorbide dinitrate
PETN=pentaerythritol tetranitrate
ETN=erythrityl tetranitrate
SNP=sodium nitroprusside
SIN-1=3-morpholinosydnonimine molsidomine
SNAP=S-nitroso-N-acetylpenicillamine
SNOG=S-Nitrosoglutathione
NOHA=N-hydroxy-L-arginine
PDE3=phosphodiesterase type III
PGE1=prostaglandin E1
cAMP=cyclic adenosine monophosphate
cGMP=cyclic guanosine monophosphate
T=Tumescence
R=Rigidity "Penis" as used herein may be interpreted to apply equally to clitoris in so far as there is substantial equivalence between penile and clitoral erectile tissue.

"Enchancing penile erection" as used herein is understood to mean increasing physical size and improving rigidity of a penis.

"Erection of good quality" and "effective erection" are used herein interchangeably to mean adequate for vaginal penetration (i.e., intromission, or intercourse).

"PDE3" and "PDEIII" are used interchangeably to describe the phosphodiesterase type three which normally degrades cAMP and is inhibitable by cGMP.

"NO donor" and "NO" producing agent' are used interchangeably in this specification and include all compounds which donate NO through biotransformation, compounds which generate NO spontaneously, compounds which spontaneously release NO, or any other compounds which otherwise generate NO.

"various forms of NO" as used herein is understood to mean any one of NO, $-NO^+$ and $NO^-$, and can include as an alternative CO (carbon monoxide).

"applying various forms of NO" as used herein includes NO donor or NO producing agents

DETAILED DESCRIPTION OF THE INVENTION

Existing patents and published literature teach little relating to the novel concepts of the invention proposed herein (pain reduction and synergistic penile erection). Some patent literature discusses the use of agents which purport to act by increasing smooth muscle levels of cyclic nucleotides, namely either cyclic adenosine monophosphate (cAMP) or cyclic guanosine monophosphate (cGMP). Agents which act by stimulating production of these cyclic nucleotides (for example PGE1 or SNP, respectively) or by inhibiting their catabolism (for example cGMP phosphodiesterase inhibitors) are discussed in relation to controlling blood vessel function, but combinations of agents which could increase both cAMP and cGMP simultaneously and affect (reduce or avoid) pain are not discussed.

Scientific literature dealing with agents affecting cyclic nucleotide levels and the relationship of these effects to prostanoid-mediated pain is limited. Those studies which have been conducted to examine the issue of analgesia and the use of nitric oxide (NO) as an analgesic have been conducted in a rat hind paw model (European Journal of Pharmacology, Vol 186:289 (1991); Vol 217:207 (1992); Vol 201:121 (1991) and Vol 217:225 (1992)). Such studies indicate that a nitric oxide donor can act as an analgesic in the case of hyperalgesia induced by subcutaneously applied prostaglandin E2 (PGE2). However, there is no suggestion that NO donors would have any application in the field of erectile tissue dysfunction in connection with the management of pain associated with the use of prostaglandins. Indicated uses of NO donors in connection with erectile tissue dysfunction are for vasorelaxation (see discussion in U.S. Pat. No. 5,278,192). Indeed, in a study in 1993 by Brock et al (J. Urology, Vol. 150:864, (1993)) although vasorelaxation effects of sodium nitroprusside (SNP) were reported, the use of nitric oxide and nitric oxide producing agents is discouraged as significant hypotension may be induced by intracavernosal injection of such agents at doses sufficient to produce an erection. Further, U.S. Pat. No. 5,439,938 teaches methods and devices for reversing pain associated with priapism by providing NO synthase inhibitors.

Scientific literature concerning non-penile vasodilation supports our understanding of our invention that use of enhancers of the level of cGMP such as NO (which is believed to activate guanylyl cyclase) and enhancers of the level of cAMP such as prostaglandins (which is believed to activate adenylyl cyclase), can cause synergistic vasodilation (Molecular Pharmacology Vol 37:671 (1990); and in the European Journal of Pharmacology, Vol 192:235 (1991); Vol 191:471 (1990); and Vol 250:477 (1993)). The mechanism of the synergism has been hypothesized to be due to overall increased concentrations of cAMP through cGMP's inhibitory effects on phosphodiesterase type III (PDE3). PDE3 is believed to be responsible for the breakdown of cAMP. However there is no indication what effect such combinations would have on pain. Indeed, in view of the literature cited above concerning reversing priapism with NO synthase inhibitors, as well as the studies on analgesia and NO, increases in cAMP, either by means of increasing the presence of cAMP or by decreasing the breakdown of cAMP, would be expected to increase pain. There is also no literature which considers what impact, if any, such combination of agents in the corpus cavernosum would have on erectile function. Notwithstanding this, the use of combination therapies to achieve erection while attempting to avoid pain are known, but rely on additive vasodilation.

For example, a report by B. vonheyden et al.(Journal of Urology Vol. 149:1288 (1993)) indicates that intracavernosal therapy supports the use of prostaglandins (PGE1) introduced intracavernosally by injection (ICI). This study reports the use of PGE1 and papaverine and phentolamine in combination as a means of reducing one of the main side effects of using prostaglandins, namely pain. As discussed above, pain occurs in 40–45% of patients during prolonged use of PGE1. Although the cause of the pain is at present unknown, a report in the European Journal of Pharmacology (Vol 217:225, 1992) suggests that sensitization of nociceptors by PGE2 or sympathomimetic amines is due to activation of adenylate cyclase with a consequent increase in intracellular cAMP/$Ca^2$ levels. The suggestion made in the vonHeyden study is that to reduce the likelihood of occurrence and degree of pain, it is appropriate to reduce the level of prostaglandins used. This concept simply applies conventional principles of pharmacology, namely, less drug will provoke less effect, in this case pain. The loss in effect on erectile function by reducing the prostaglandins is compensated by the other agents in the combination therapy. While reference is made to the possibility of synergism between PGE1, papaverine and phentolamine, nothing is taught regarding the use of a second agent which has the effect of reducing the pain associated with use of prostaglandins while concomitantly providing a synergistic erectile response. This art teaches use of PGE1 at concentrations on the order of 10–40 μg (the previously accepted treatment range) causes pain.

A study by Hempelmann, R. G. et al (European Journal of Pharmacology Vol 276:277 (1995)) addresses the question of whether vasoactive intestinal peptide (VIP) and NO donors are capable of exerting a synergistic effect in isolated cavernous artery and corpus cavernosum. The results of the study indicated that VIP is not capable of causing concentration dependent relaxation responses, whereas, in contrast, 3-morpholinosydnonimine molsidomine (SIN-1) has the capacity to induce complete relaxations. The study demonstrated that VIP and SIN1 exert non-synergistic independent relaxant effects in human cavernous artery and cavernosal smooth muscle. Consequently the study argues against a combined therapeutic administration of these two agents.

A further study by Martinez-Pineiro, L. et al (Journal of Urology Vol 153:1487 (1995)) discusses intracavernous injection of vasoactive drugs and enumerates those commonly known agents such as papaverine, phentolamine and PGE1 and the possibility of therapy with a combination of these drugs. In the discussion portion of this report, there is consideration of the mechanism of action of prostaglandin-like agents in causing pain and it is theorized that activation is through adenylyl cyclase, which would have the effect of increasing levels of cAMP. This is in accordance with the suggested molecular basis for pain as discussed above in respect of NO. However no firm conclusions are reached with respect to dealing with the side effects of such therapies or the associated pain.

Consequently, the use of combinations have not been successful at alleviating the pain associated with the use of substances like PGE1. Specifically, the use of prostaglandin compounds with non-specific acting compounds such as papaverine and phentolamine have been shown to be associated with an increased incidence of priapism with pain. In contrast, the combination therapy of the present invention induces effective erections while reducing or entirely avoiding pain.

Experimental

Two series of experiments were carried out with the results presented below. The first series (A. No prior PGE1) was a group of patients who did not have prior use of $PGE1_1$ and thus there was little expectation of a pain response in respect of administration of PGE1. The expectation of a pain response in this series of patients, based on the literature is a frequency of pain per injection in the order of 3 to 10 percent. Although this may be within the standard deviation of the experiments as demonstrated below, the results indicate that none of the patients experienced any pain. Not only was there no pain, the response of PGE1 was significantly enhanced by use of the NO donor, (in this case sodium nitroprusside (SNP)). This enhanced response is normally associated with higher doses of PGE1 and with such higher doses, there is associated pain.

The second series of patients (B. Prior use of PGE1) who were part of this study had a clinical history of pain in association with the use of prostaglandin therapy wherein this therapy was used for the purpose of obtaining penile erection. As demonstrated below, the results from this series indicate that all of the patients upon receiving a reduced dose of PGE1 experienced reduced pain or no pain at all and enhanced penile erection notwithstanding the reduction in dose of PGE1.

General Methods Measurements were made in a clinical erectile dysfunction (ED) laboratory in patients with previously diagnosed ED. These patients were being evaluated for the purpose of optimization of their intracavernous injection dosing. All men were assessed using the Queen's University Human Sexuality Group Protocol (Kingston, Ontario, Canada).

A. No prior PGE1

Patients were fitted with the Rigiscan™ tumescence and rigidity recording device. The patients were injected with the intracavernous (IC) drug using up to 2 different doses (PGE1 alone or in combination with sodium nitroprusside (SNP50 μg)) and monitored in real-time for their erectile response. Patients were only given a second injection (higher dose PGE1) if the response to the first injection was less than 70% of maximum tumescence and rigidity. In addition, patients were asked to report any occurrence of pain specific to the injection, but not related to acute discomfort associated with the needle prick.

Initial Inclusions: Men with known erectile dysfunction characterized by a three month history.

Exclusions

1. Patients whom responded to IC injection with full tumescence at the lowest dose of PGE1 alone.
2. Patients in whom there were no significant responses at any dose (revealing a high degree of organic disease).
3. Patients in whom there was a technical problem with measurements (incomplete data).

Two Phases of the Evaluation of Optimization Protocol

Phase 1: (n=9)
1st visit—IC injection PGE1 5 μg IC
2nd visit—IC injection PGE1 5 μg+SNP 50 μg Phase 2: (n=12)
1st visit—IC injection PGE1 5 μg IC—then (15 mins) PGE1 15 μg IC
2nd visit—IC injection PGE1 5 μg+SNP 50 μg—then (15 min) PGE1 15 μg+SNP 50 μg

RESULTS

Erectile Responses: Phase 1 was conducted to validate the known effects of low dose PGE1 and to confirm the safety margin using SNP (Lue et al, Journal of Urology 150: 864–867 (1993)). In 4 of 9 patients there was a poor response to both injections. 2/9 experienced full tumescence with the lowest dose of PGE1 alone. 3/9 showed moderate to substantial improvement with the combination. In only 1 patient, having a moderate response to low dose PGE1 alone, was there was no enhancement. The data from this study confirmed that in a number of patients higher doses of PGE1 alone or in combination are required to induce an erectile response.

Figure 1:
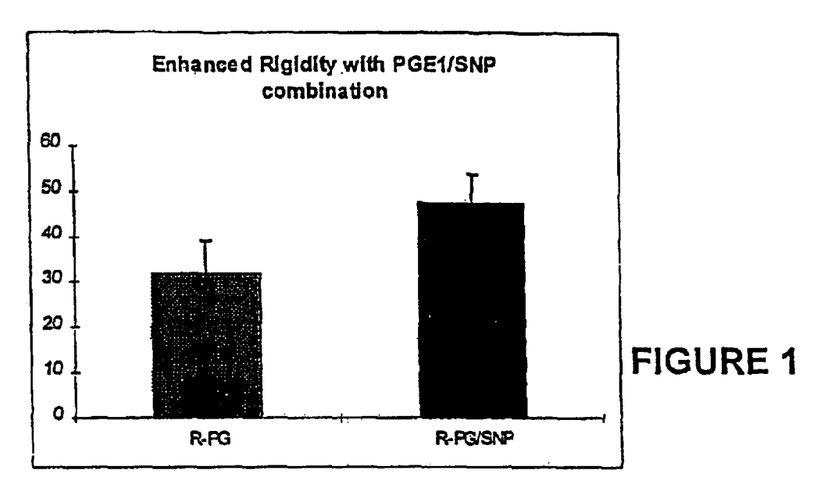
FIG. 1 is a bar graph which demonstrates enhanced penile rigidity with PGE1 in combination with SNP when compared to a dose of PGE1 only.
Figure 2:
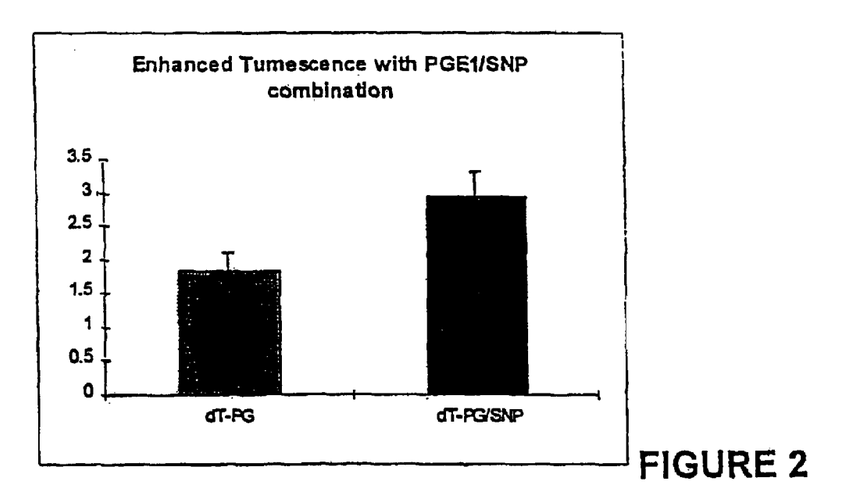
FIG. 2 is a bar graph demonstrating tumescence results from patients receiving PGE1 in comparison with patients receiving PGE1 and sodium nitroprusside in combination.

Based on this finding, the protocol was changed to include higher doses of PGE1. In the Phase 2 protocol four formulations were developed: The first PGE (5 μg in 1 ml saline), the second, a higher concentration of PGE1 (15 ug in 1 ml saline), the third PGE1+SNP (5 ug+50 ug in 1 ml saline) and the fourth PGE1+SNP (15 ug+50 ug in 1 ml saline). In the phase 2 study, 12 patients were assessed. Full data are available on 10 of these (see below FIG. 1, where the ordinate represents % rigidity units, and FIG. 2). 3 of these 10 developed full responses to the 5+15 μg PGE1 alone. For the remaining 7 patients there was significant enhancement in all patients (p<0.05) when combined with SNP. None of these patients experienced any drug-related pain with these treatments.

B. Prior use of PGE1

The patients who were part of this study had a clinical history of pain in association with the use of prostaglandin therapy wherein this therapy was used for the purpose of obtaining penile erection. As detailed below, one of three different modes of administration of NO producing agents were used depending upon the patient. In particular, each of these individuals received a NO donor either through the use of a nitrospray such as Nitrolingual™ or a transdermal patch delivering a NO donor compound, and in three cases, a combination of PGE1 and 50 μg of SNP (in saline or phosphate buffered saline (PBS)). Results of these treatments are detailed below.

Case No. 1

DB, aged fifty-five, underwent a radical perineal prostatectomy in October, 1996. This patient was seen in Injection Clinic in February, 1997. Injection of 5 μg PGE1 and then a further 5 μg PGE1 was given at a fifteen minute intervals. After the second injection, he sustained aching pain in his penis for a duration of approximately fifteen minutes. DB used a nitrospray (Nitrolingual™) on a regular basis and was asked to use it at the time of injection with PGE1 and record the response in his penis. He took one oral spray and reported relief within two minutes of all penile discomfort. The erection was of good quality and was sustained. The patient reported that this erection would be adequate for intercourse. The erection was witnessed.

Case No. 2

CC, aged seventy-one, underwent radical perineal prostatectomy in January, 1996 and was seen in October, 1996 and is currently using 10 μg PGE1 at home with pain and a poor response. He was seen in the Clinic and prescribed a transdermal patch delivering an NO donor compound at a rate of 0.2 mg/hour placed twenty minutes before injection. 10 μg PGE1 was injected. The patient reported no pain and obtained an erection good enough that the couple wanted to be left alone. The erection was witnessed.

Case No. 3

GH, aged fifty-four, underwent radical perineal prostatectomy in October, 1996. During the course of his recovery he reported some spontaneous and some pharmacologically induced erections. He was seen in February, 1997. The patient reported that home use of PGE1 produces penile ache unless preceded with the use of the Nitropatch 0.2 mg/hour ten minutes prior to injection or sexual response.

Case No 4

JB, aged fifty-four, underwent radical perineal prostatectomy in September, 1995 reports pain with intracavernosal injection of PGE1. In May, 1996, he used 20 μg PGE1 with SNP 50 μg and he reported the SNP "decreased the pain".

Case No. 5

Another JB, aged seventy-one, multi-factorial erectile dysfunction reports pain with intracavernosal injection of PGE1 lasting three to four hours. In May, 1996 he received 20 μg PGE1 with 50 μg SNP, repeated fifteen minutes later (20 μg PGE1+50 μg SNP) producing no burning and a response judged by the patient and an experienced nurse to be at least 75%, i.e., a full erection.

Case No. 6

TW, aged fifty-eight, radical perineal prostatectomy in 1996 reported frequent pain at home with PGE1. In March, 1997, 10 μg PGE1 and 50 μg SNP repeated fifteen minutes later with 10 μg PGE1 and 50 μg SNP produced no burning and substantial efficacy, namely a full erectile response.

The concentration of glyceryl trinitrate (the typical form of NO donor derived from Nitrospray or Nitropatches) has been reported in the literature for such delivery routes to be in the order of 200 to 400 picograms per milliliter (pg/ml) of plasma (Sun et al, J. Clin. Pharmacol. (35) 390, 1995).

While the routes of administration of PGE1 and the NO donors reported here include IC injection of prostaglandin and IC injection of NO donor, or by nasal spray or by patch, the present invention includes administration by means of topical creams, pharmaceutically acceptable organic and inorganic carrier substances suitable for parenteral, enteral, intraurethral or intranasal application which do not deleteriously react with the active compounds.

Compositions of the invention are administered to subjects in a biologically compatible form suitable for pharmaceutical administration in vivo. By "biologically compatible form suitable for administration in vivo" is meant a form of the active compounds of the invention to be administered in which any toxic effects are outweighed by the therapeutic effects of the active compounds of the invention. The term subject is intended to include living organisms in which a response can be elicited, e.g., mammals. Examples of subjects include humans, dogs, cats, mice, rats, and transgenic species thereof.

Administration of a therapeutically active amount of the therapeutic compositions of the present invention is defined as an amount effective, at dosages and for periods of time necessary to achieve the desired result. For example, a therapeutically active amount of active compounds of the invention may vary according to factors such as the disease state, age, sex, and weight of the individual, and the ability of an agent or combination of agents of the invention to elicit a desired response in the individual. Dosage regimens may be adjusted to provide the optimum therapeutic response. For example, several divided doses may be administered or the dose may be proportionally reduced as indicated by the exigencies of the therapeutic situation.

The active compounds (e.g., SNP and PGE1) may be administered in a convenient manner such as by injection (subcutaneous, intravenous, intracavernous, etc.), oral administration, inhalation, transdermal application, rectal administration, urethral administration or intracavemous introduction. Depending on the route of administration, the active compound or compounds may be coated in a material to protect the compound(s) from the action of enzymes, acids and other natural conditions which may inactivate the compound(s), or facilitate or enable delivery of said compound(s).

A SNP and PGE1 composition or as separate agents can be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions and vehicles of solid, liquid or gas phase. To administer an agent or agents of the present invention by other than parenteral administration, it may be necessary to coat the active compound(s) of the invention with, or co-administer the agent or agents of the present invention with, a material to prevent its inactivation. Liposomes include water-in-oil-in-water emulsions as well as conventional liposomes (Strejan et al, J. Neuroimmunol 7:27 (1984)). The active compound(s) may also be administered parenterally or intraperitoneally. Dispersions can also be prepared in glycerol, liquid polyethylene glycols, and mixtures thereof in oils and other solutions. Under ordinary conditions of storage and use, these preparations may contain a preservative to prevent the growth of microorganisms, stability enhancers and compounds to preserve physical characteristics that are needed for appropriate delivery.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, and sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating active compounds (e.g., SNP and PGE1) in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of an active ingredient of the invention plus any additional desired ingredient from a previously sterile-filtered solution thereof.

When an active compound is suitably protected, as described above, the composition may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such medica and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the therapeutic treatment of individuals.

While it is described and understood that the method of this invention includes the combination of NO donors and PGE1, the invention includes the combination of NO donors and other analgesics such as opiates, non-steroidal anti-inflammatory drugs, such as ibuprofen, naproxen, and mefanamic acid, to produce a synergistic lowering of pain.

While the invention has been particularly shown and described with reference to certain embodiments, it will be understood by those skilled in the art that various other changes in form and detail may be made without departing from the spirit and scope of the invention.

All paper references and patents referred to in this specification are incorporated in totality by reference herein.

We claim:

1. A method of decreasing pain associated with use of prostaglandins for treatment of erectile tissue dysfunction comprising administering to a human in need thereof an effective amount of prostaglandin and at least one NO producing agent at a low dose, which decreases pain associated with prostaglandin use, wherein said low dose of said at least one NO producing agent is a unit dose of about 0.88 μmole or less, and wherein the administration is therapeutically synergistic in the treatment of erectile tissue dysfunction, and is not an intraurethral administration.

2. The method of claim 1 wherein the human is male.

3. The method of claim 1 wherein the human is female.

4. The method of claim 1 wherein the NO producing agent inhibits a cyclic nucleotide phosphodiesterase.

5. The method of claim 4 wherein the cyclic nucleotide phosphodiesterase is PDE3.

6. The method of claim 1 wherein the NO producing agent is delivered by a route selected from the group consisting of oral administration, intravenous administration, subentaneous administration, inhalation or intranasal administration, transdermal application, topical application, rectal administration, and intracavernous introduction.

7. The method of claim 1 wherein two agents are administered.

8. The method of claim 1 wherein the NO producing agent is selected from the group consisting of glyceryl trinitrate, isosorbide 5-mononitrate, isosorbide dinitrate, pentaerythritol tetranitrate, erythrityl tetranitrate, sodium nitroprusside, 3-morpholinosydnonimine, molsidomine, S-nitroso-N-acetylpenicillamine, S-nitrosoglutathione, N-hydroxy-L-arginine, S,S-dinitrosodithiol and NO gas.

9. The method of claim 1 wherein the NO producing agent is glyceryl trinitrate.

10. The method of claim 6 wherein the NO producing agent is delivered by inhalation.

11. The method of claim 6 wherein the NO producing agent is delivered by transdermal application.

12. The method of claim 6 wherein the NO producing agent is delivered by oral administration.

13. The method of claim 1 wherein said NO producing agent augments the action of cGMP.

14. The method of claim 1 wherein said NO agent is sodium nitroprusside and said effective amount of prostaglandin is an effective amount of prostaglandin E1.

15. The method of claim 1 wherein said at least one NO producing agent is a unit dose of 200 µg or less.

16. The method of claim 1 wherein the mole ratio of said effective amount of prostaglandin to said at least one NO producing agent is about 1 to 12.

17. The method of claim 1 wherein the mole ratio of said effective amount of prostaglandin to said at least one NO producing agent is about 1 to 4.

18. The method of claim 1 wherein the mole ratio of said effective amount of prostaglandin to said at least one NO producing agent is about 1 to 3.

19. The method of claim 14 wherein said sodium nitroprusside administered is about 50 µg and said effective amount of prostaglandin (PGE1) administered is about 5–20 µg.

20. The method of claim 6 wherein said NO producing agent is delivered by intracavernous administration.

* * * * *

UNITED STATES PATENT AND TRADEMARK OFFICE
CERTIFICATE OF CORRECTION

PATENT NO. : 6,747,063 B2
DATED : June 8, 2004
INVENTOR(S) : Adams et al.

It is certified that error appears in the above-identified patent and that said Letters Patent is hereby corrected as shown below:

Column 12,
Line 55, replace "subenta-" with -- subcuta- --.

Signed and Sealed this

Tenth Day of May, 2005

JON W. DUDAS
*Director of the United States Patent and Trademark Office*